United States Patent [19]

Aoki et al.

[11] Patent Number: 4,551,168
[45] Date of Patent: Nov. 5, 1985

[54] HERBICIDAL 2-(1,3,5-1H-TRIAZIN-2-ONE)-TETRAHYDROBENZOTHIAZOLE DERIVATIVES, AND COMPOSITIONS THEREFOR

[75] Inventors: Katsumichi Aoki; Takafumi Shida; Satoru Kumazawa; Susumu Shimizu; Yohichi Kanda; Keigo Satake; Shiro Yamazaki; Hiroyasu Shinkawa; Tsuneaki Chida; Hideo Arabori; Takeo Watanabe, all of Iwaki, Japan

[73] Assignee: Kureha Kagaku Kogyo Kabushiki Kaisha, Tokyo, Japan

[21] Appl. No.: 596,928

[22] Filed: Apr. 5, 1984

[30] Foreign Application Priority Data

Apr. 8, 1983 [JP] Japan ................... 58-61927

[51] Int. Cl.[4] .................. C07D 417/04; A01N 43/64; A01N 43/78
[52] U.S. Cl. .............................. 71/90; 71/93; 544/200
[58] Field of Search ................ 544/200; 71/90, 93

[56] References Cited

U.S. PATENT DOCUMENTS

| | | | |
|---|---|---|---|
| 3,379,725 | 12/1984 | Schäfer et al. | 544/220 |
| 3,696,101 | 10/1972 | Litt et al. | 544/220 |
| 3,780,051 | 12/1972 | Litt et al. | 544/220 |

FOREIGN PATENT DOCUMENTS

| | | | |
|---|---|---|---|
| 2402909 | 8/1975 | Fed. Rep. of Germany | 544/220 |
| 2259825 | 8/1975 | France | 544/220 |
| 1447182 | 8/1976 | United Kingdom | 544/220 |

Primary Examiner—Henry R. Jiley
Assistant Examiner—J. G. Mullins
Attorney, Agent, or Firm—Austin R. Miller

[57] ABSTRACT

Disclosed herein are a derivative of tetrahydrobenzothiazole represented by the formula (I):

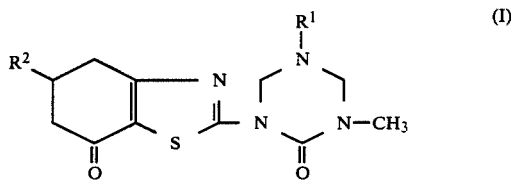

wherein $R^1$ and $R^2$ represent respectively a straight chain alkyl group having 1 to 6 carbon atoms or a branched chain alkyl group having 1 to 6 carbon atoms, and a herbicidal composition containing the same as an active ingredient.

6 Claims, 25 Drawing Figures

HERBICIDAL 2-(1,3,5-1H-TRIAZIN-2-ONE)-TETRAHYDROBENZOTHIAZOLE DERIVATIVES, AND COMPOSITIONS THEREFOR

DETAILED DESCRIPTION OF THE INVENTION

Figure 1:
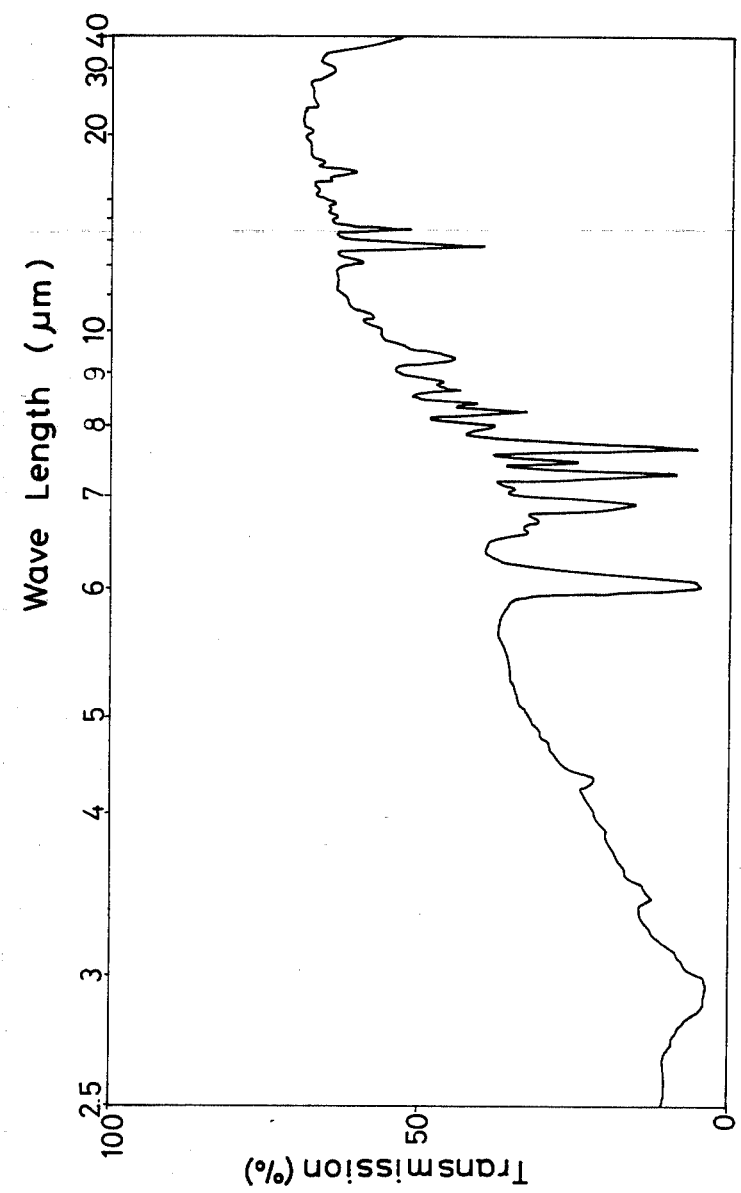

The present invention relates to a derivative of tetrahydrobenzothiazole represented by the formula (I):

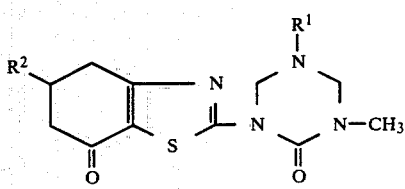

wherein $R^1$ and $R^2$ represent respectively a straight-chain alkyl group having 1 to 6 carbon atoms or a branched-chain alkyl group having 1 to 6 carbon atoms, and a herbicidal composition containing the same as an active ingredient.

The present inventors have studied for finding a compound showing an excellent activity in selectively controlling weeds such as *Echinochloa crus-galli, Poa annua, Portulaca oleracea, Cardamine flexuosa*, etc. without any phytotoxicity to crop plants such as rice, wheat, soybean and maize, and as a result, they have found that a derivative of tetrahydrobenzothiazole represented by the formula(I) shows an excellent herbicidal activity for practically controlling the weeds, and have attained to the present invention.

The compounds represented by the formula(I) are novel compounds, and of course, the physiological properties thereof have never been known. According to the herbicidal tests consisting esentially of foliar application and soil treatment, the derivatives of tetrahydrobenzothiazole according to the present invention (hereinafter referred to as "the present compounds") show an excellent herbicidal activity on broad-leaved weeds, for instance, *Stellaria media, Cardamine flexuosa* and *Portulaca oleracea*, Cyperaceous weeds, for instance, *Cyperus iria* and Gramineous weeds, for instance, those belonging to the genus Echinochloa and *Poa annua*, and particularly show strong herbicidal activity when applied on leaves and stems of these weeds. The application is carried out on crop lands such as paddy fields, upland fields, orchards, etc. and also non-crop lands.

In a first aspect of the present invention, there is provided a derivative of tetrahydrobenzothiazole represented by the formula(I):

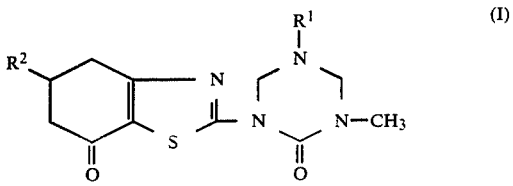

wherein $R^1$ and $R^2$ represent respectively a straight-chain alkyl group having 1 to 6 carbon atoms or a branched-chain alkyl group having 1 to 6 carbon atoms.

In a second aspect of the present invention, there is provided a herbicidal composition comprising as an active ingredient at least one derivative of tetrahydrobenzothiazole represented by the formula (I), and a diluent therefor.

In the attached Drawings, FIGS. 1 to 6 show the infrared absorption spectra of Compounds Nos. 1 to 6 according to the present invention, respectively.

The compounds of the present invention represented by the formula (I) are synthesized as follows.

One mole of the following compound represented by the formula (II):

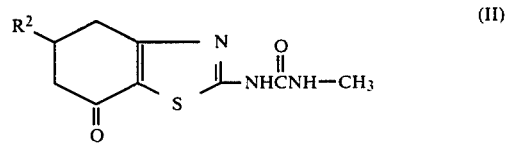

wherein $R^2$ is as defined above is brought into reaction with 2 moles of formaldehyde and 1 mole of the corresponding alkyl amine ($R^1$-$NH_2$, wherein $R^1$ is as defined above) to obtain the present compounds represented by the formula (I).

The thus obtained compounds of the present invention, represented by the formula (I) are concretely shown in Table 1 together with their respective physical properties.

TABLE 1

Figure 2:
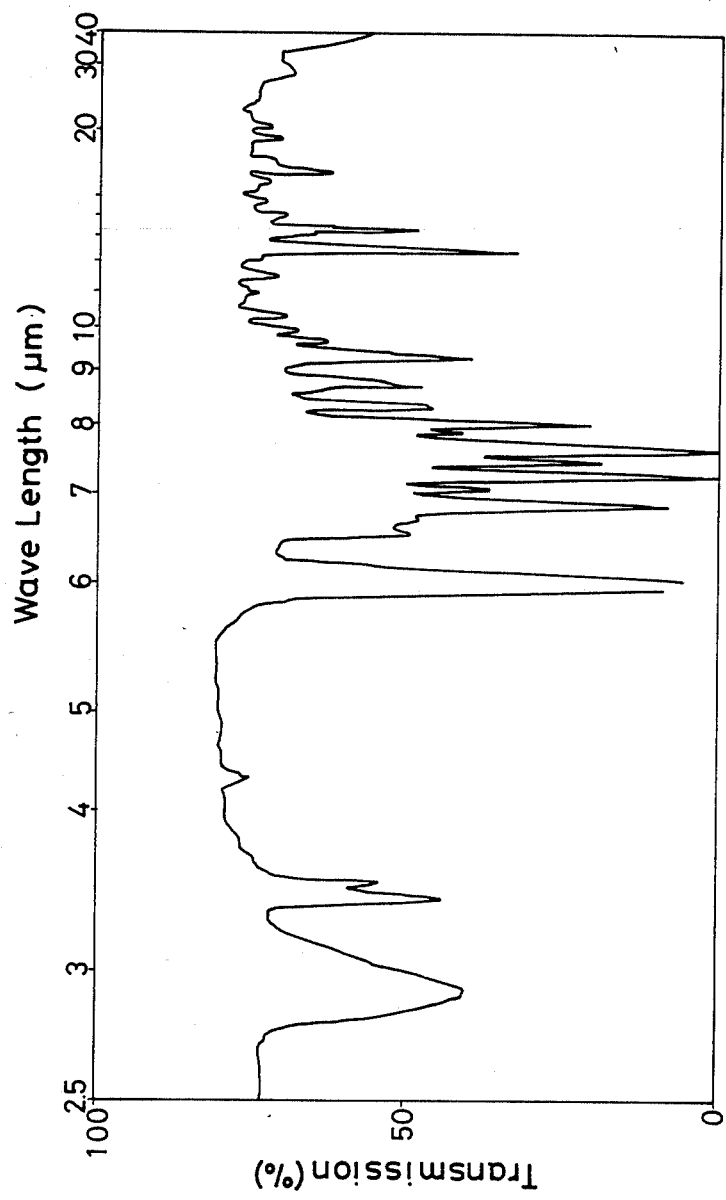
Figure 3:
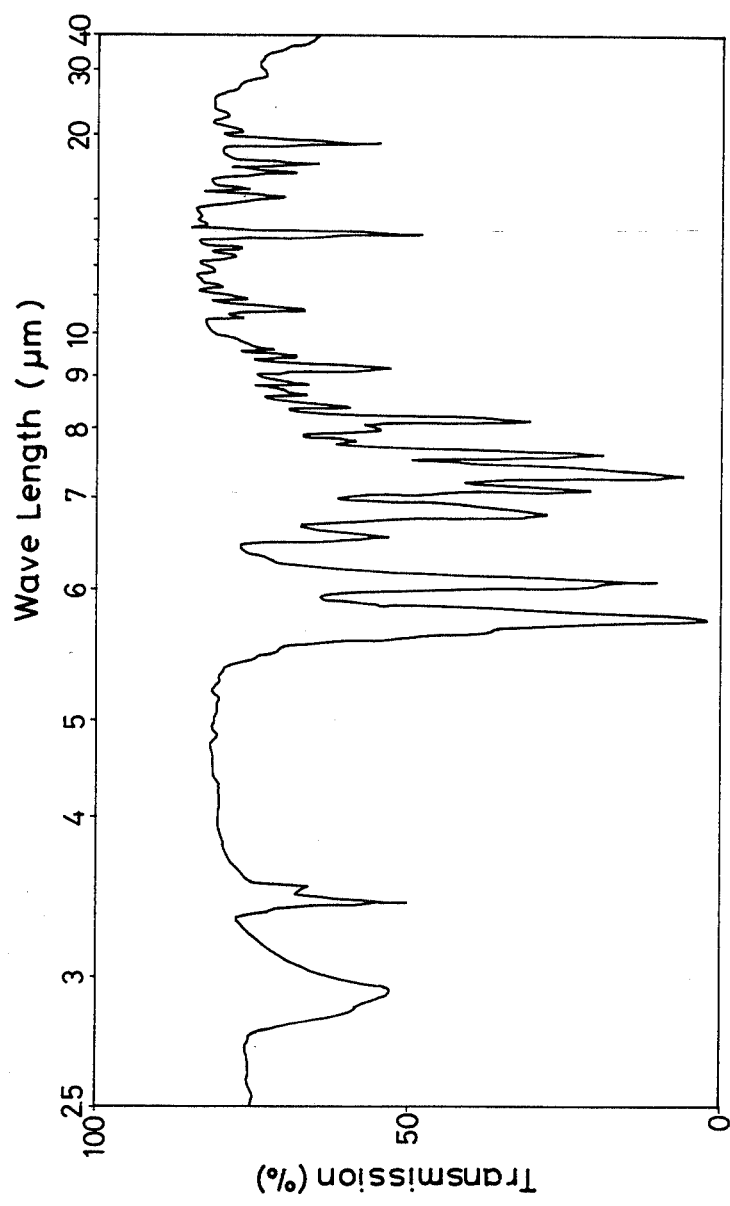
Figure 4:
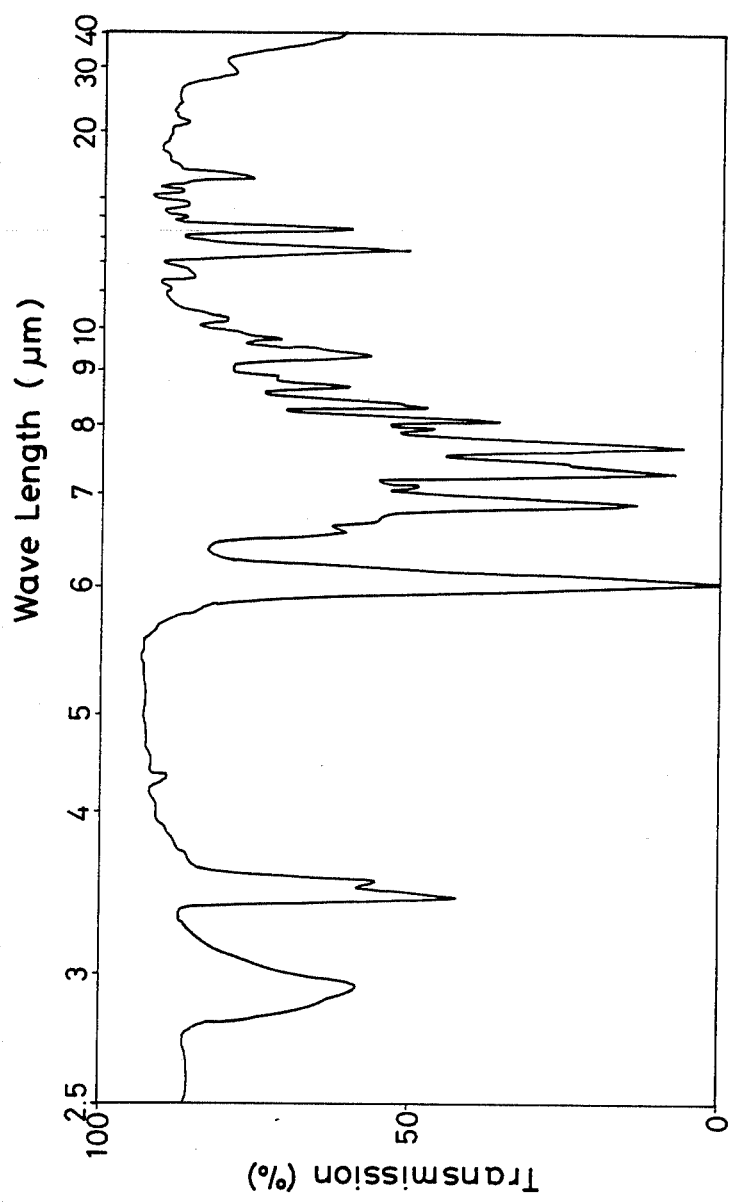
Figure 5:
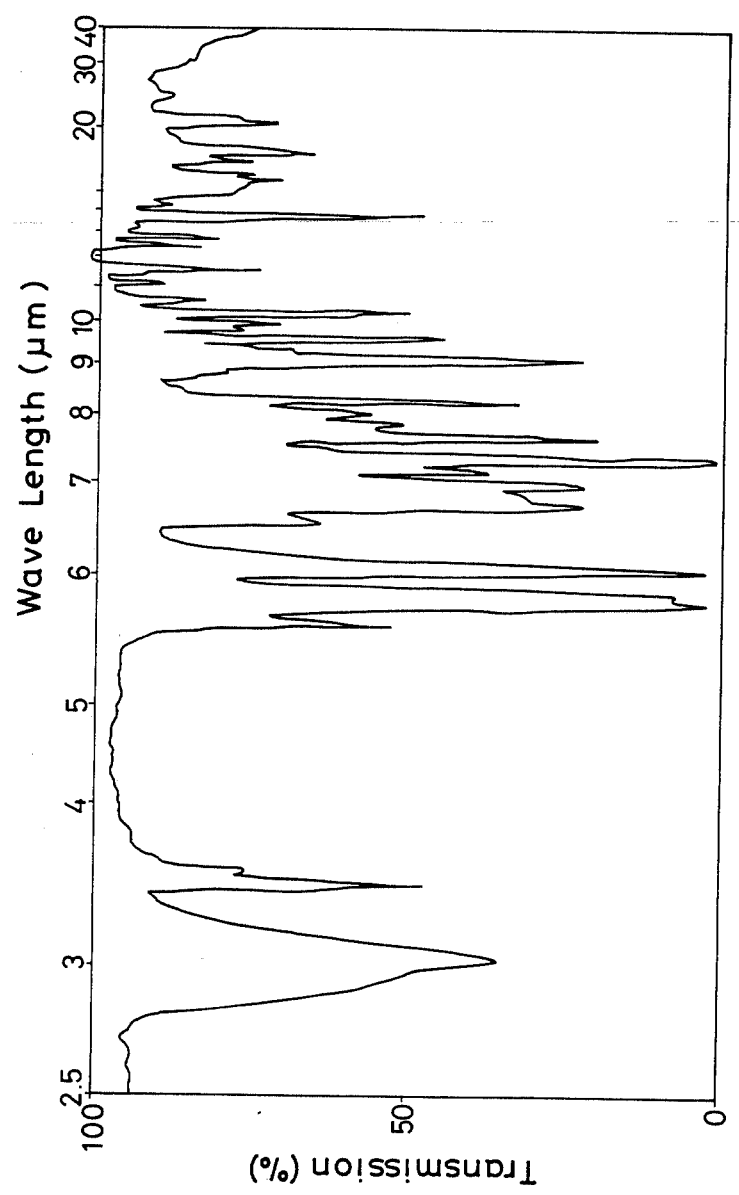
Figure 6:
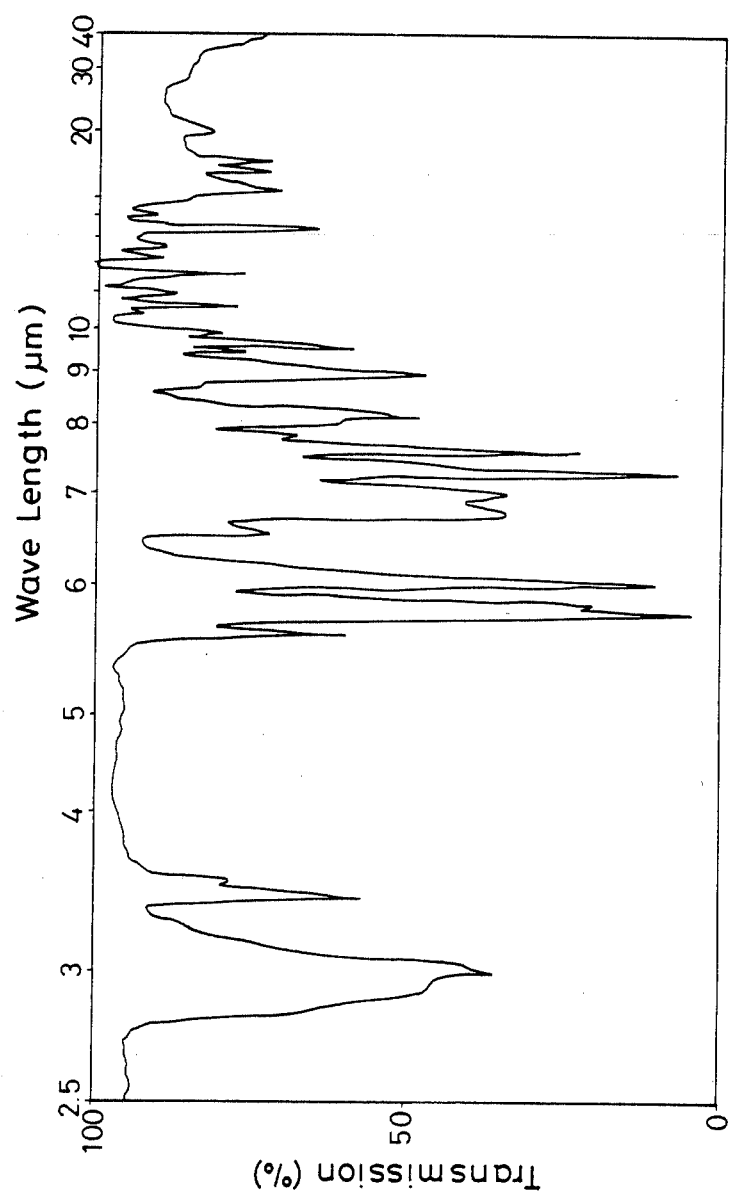
Figure 7:
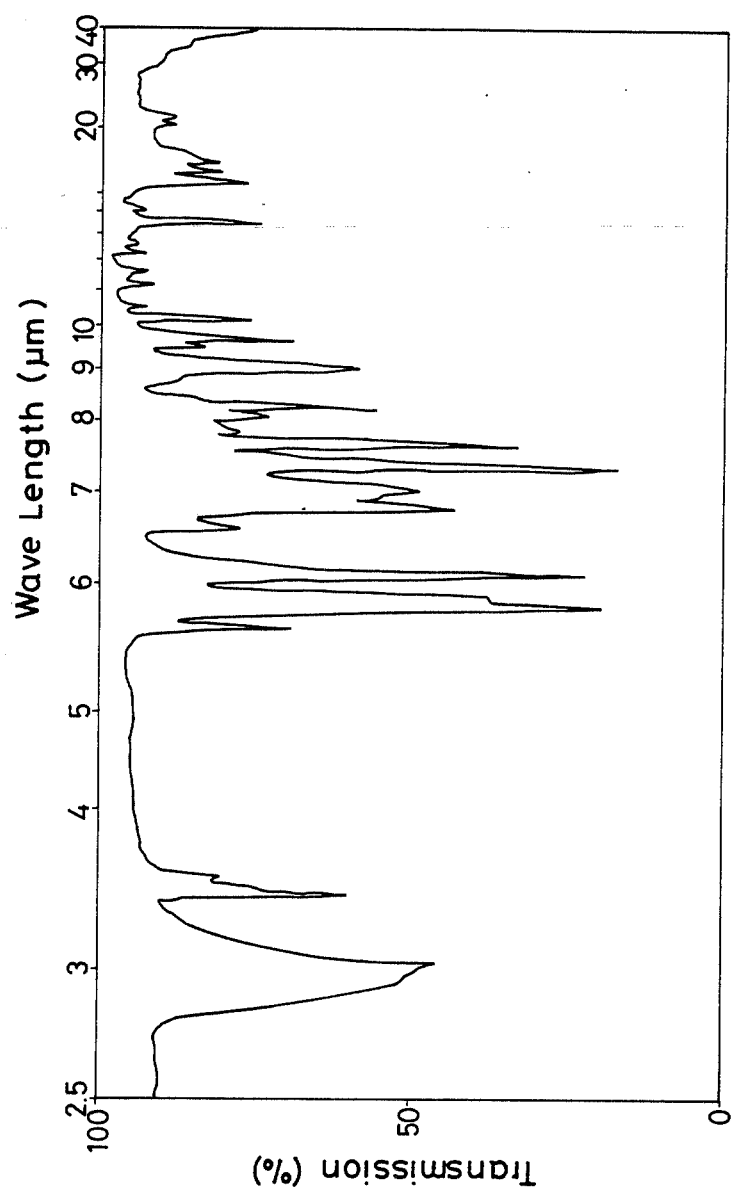
Figure 8:
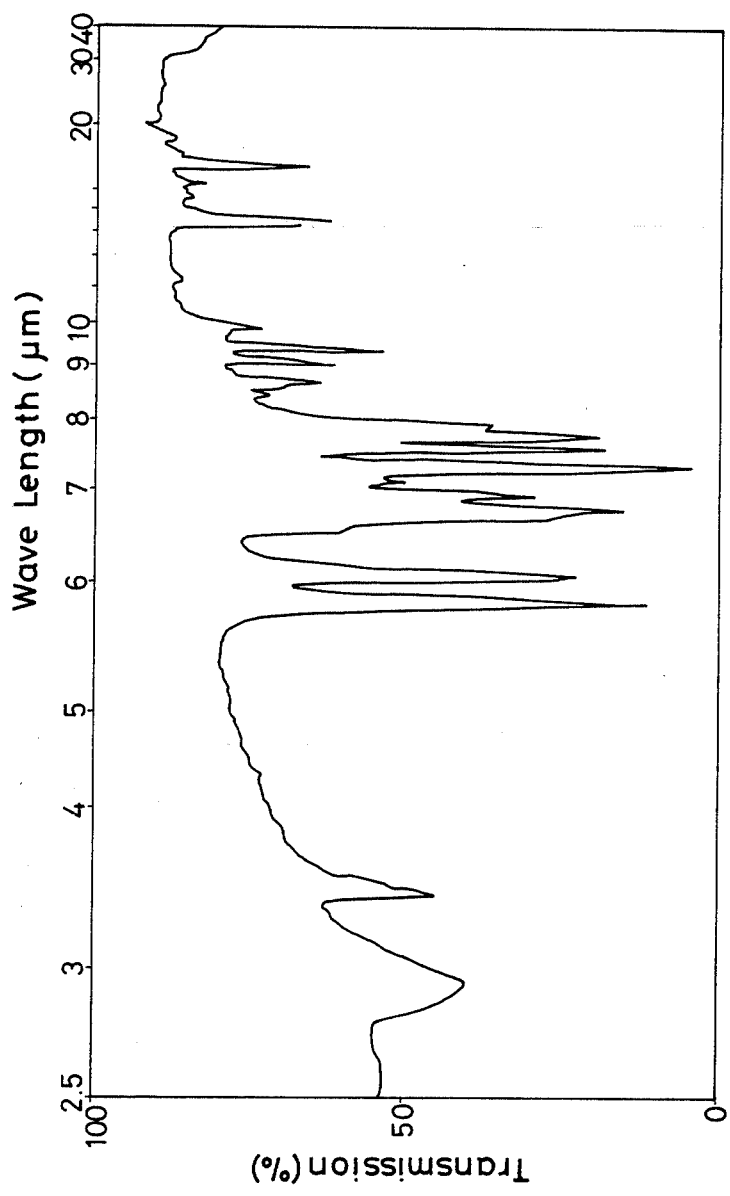
Figure 9:
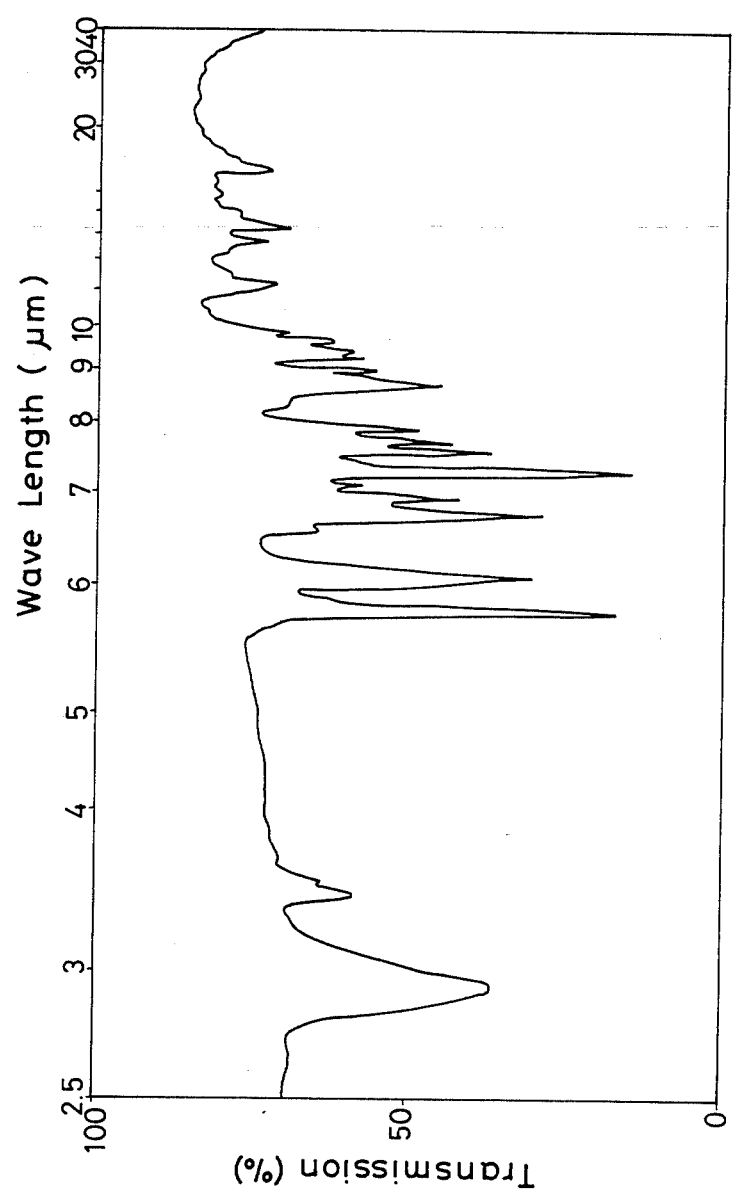
Figure 10:
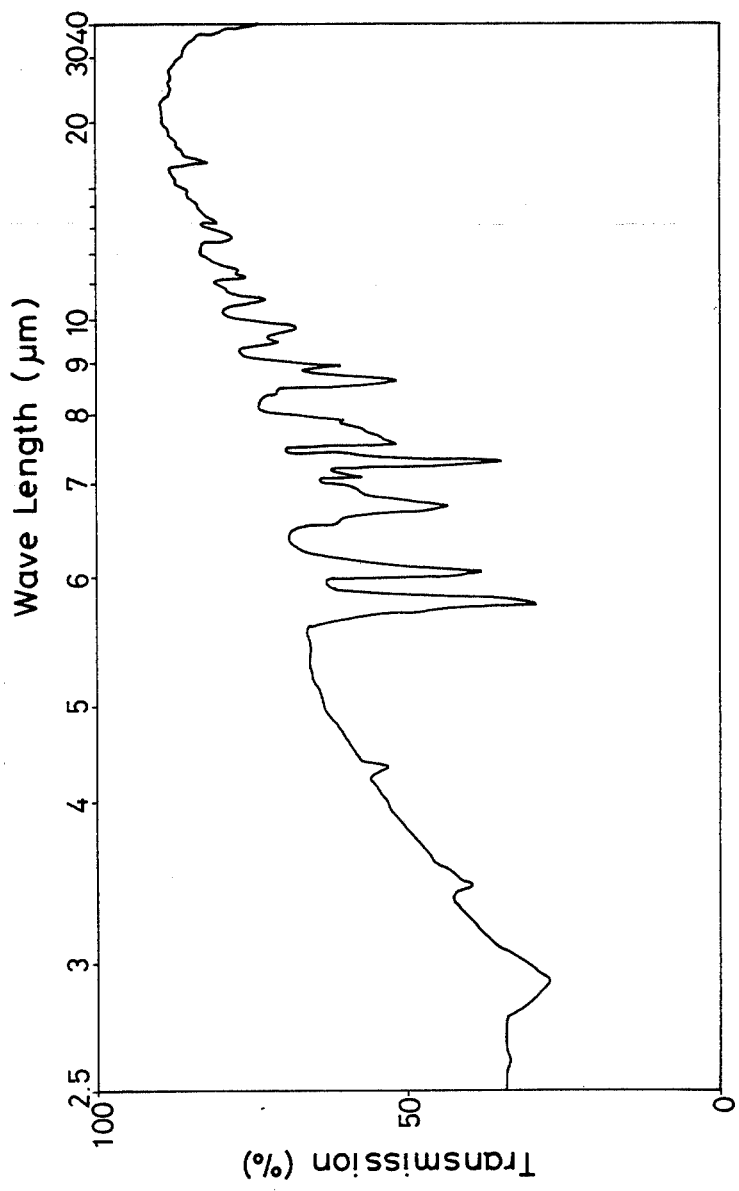
Figure 11:
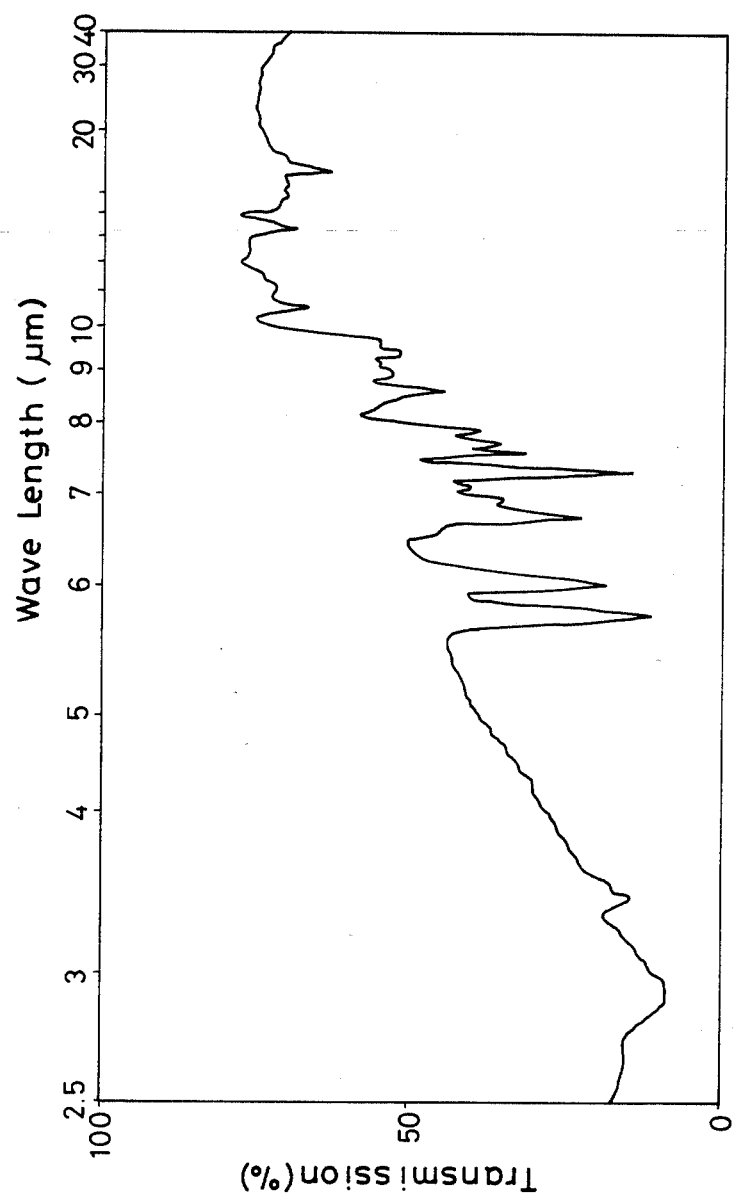
Figure 12:
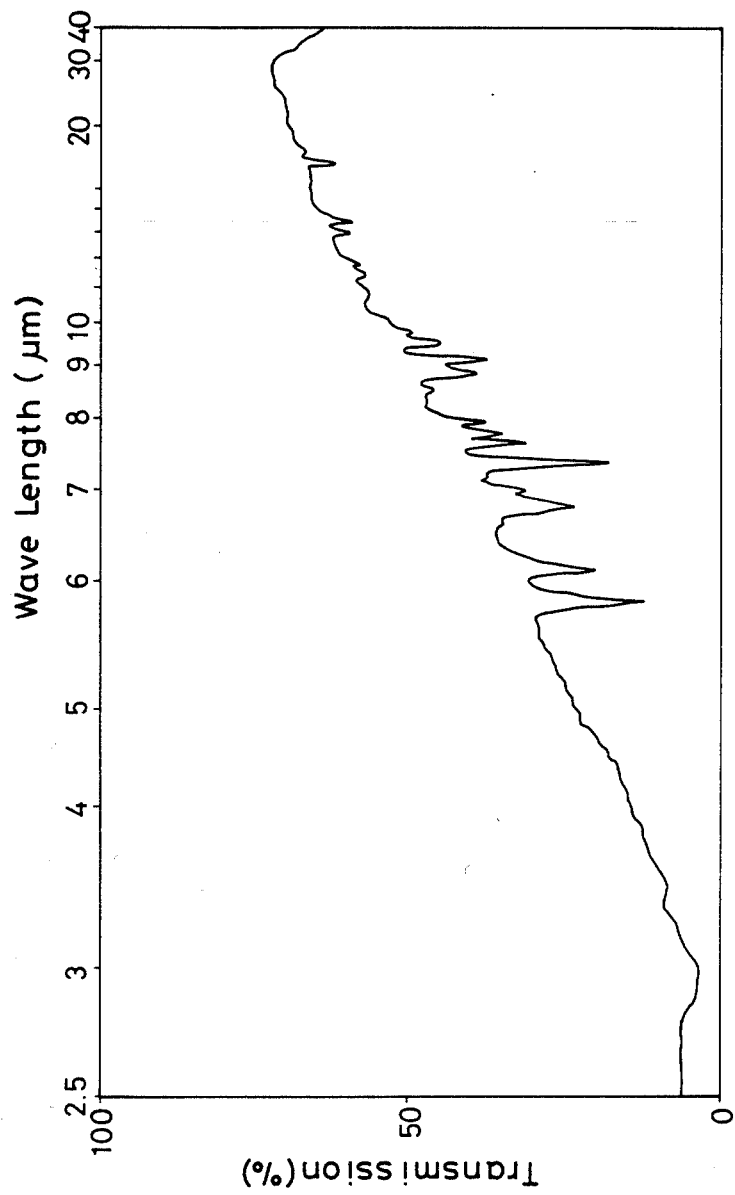
Figure 13:
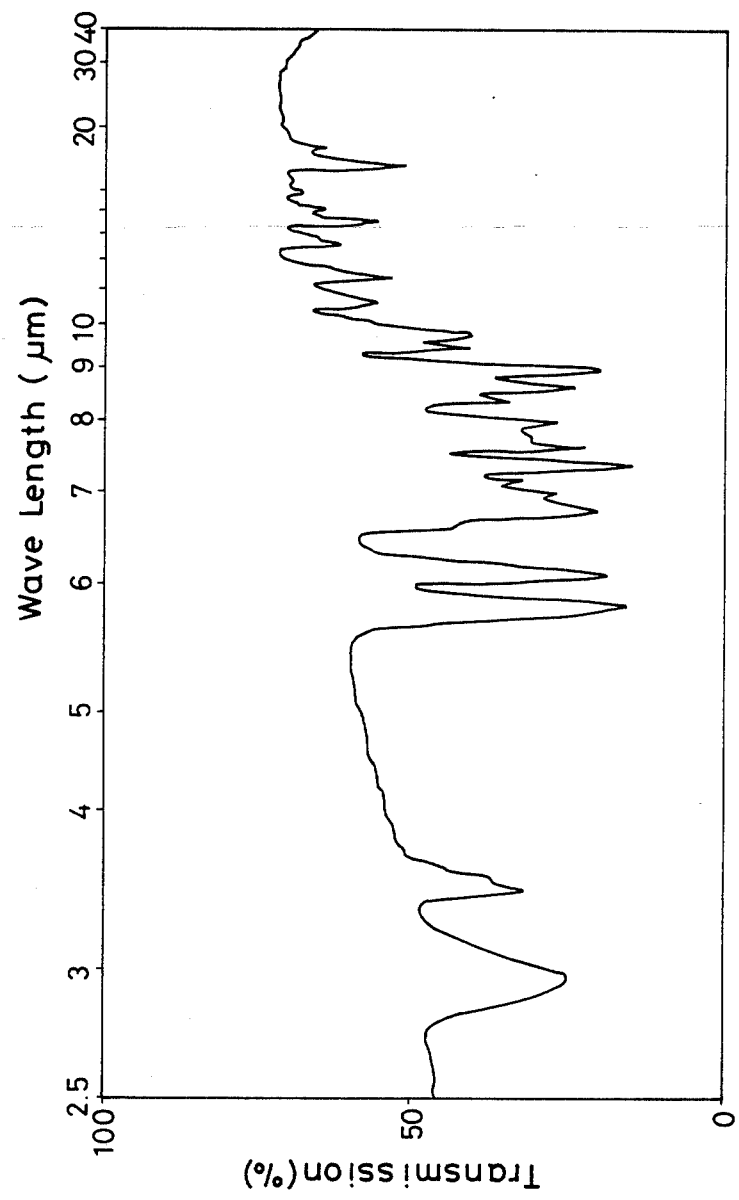
Figure 14:
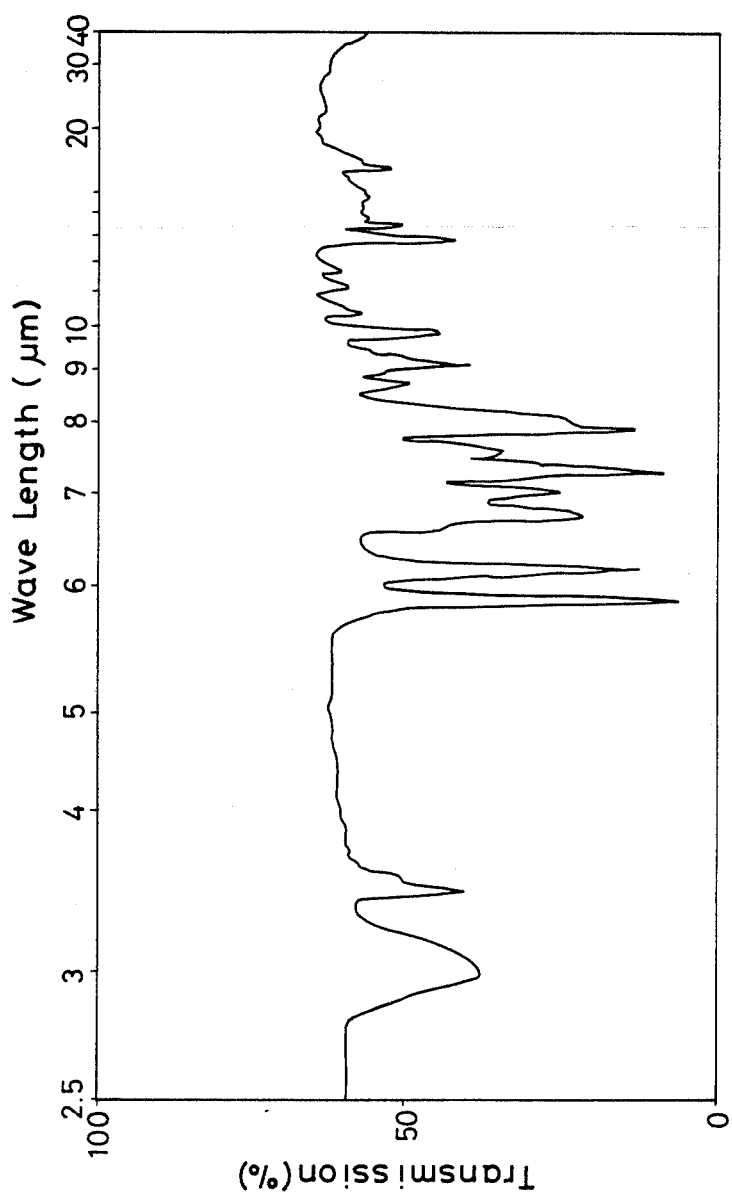
Figure 15:
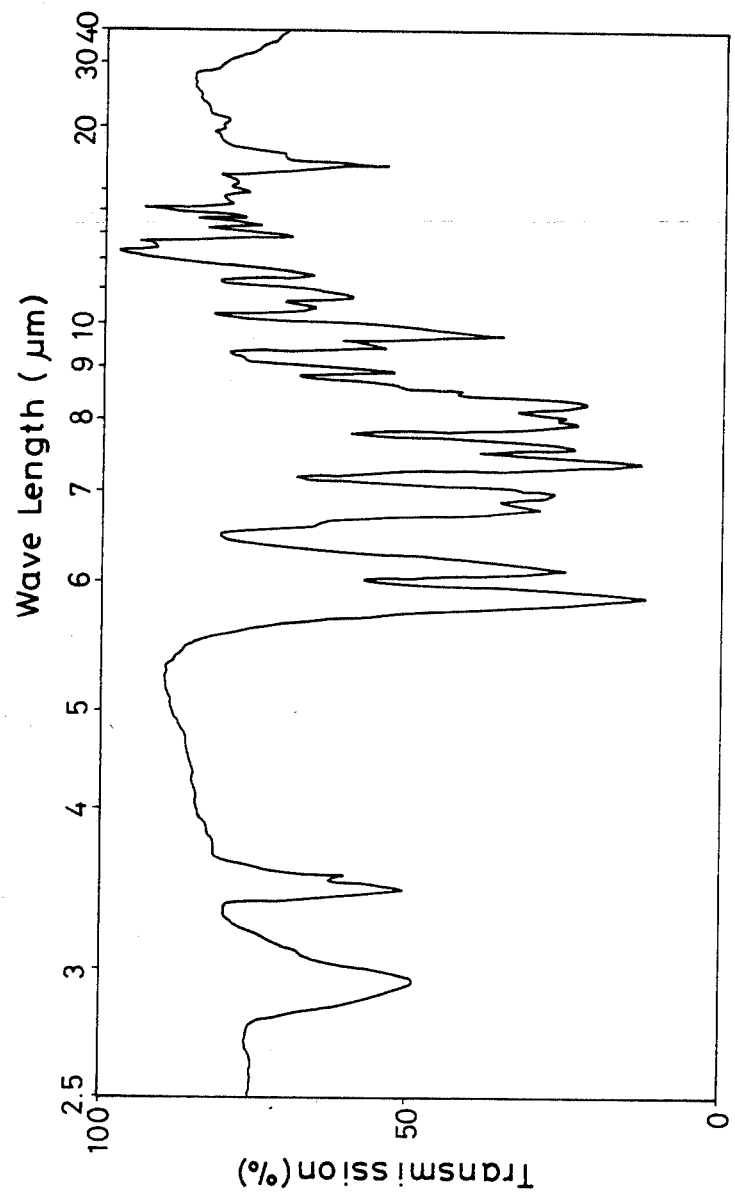
Figure 16:
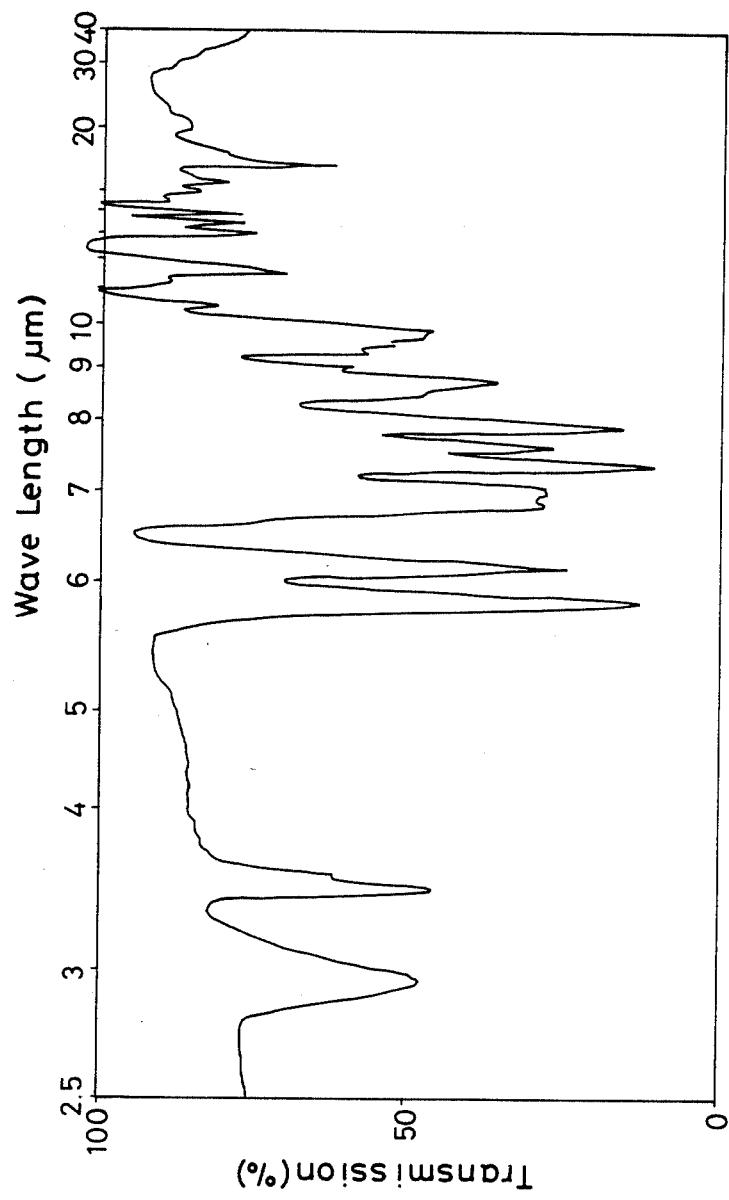
Figure 17:
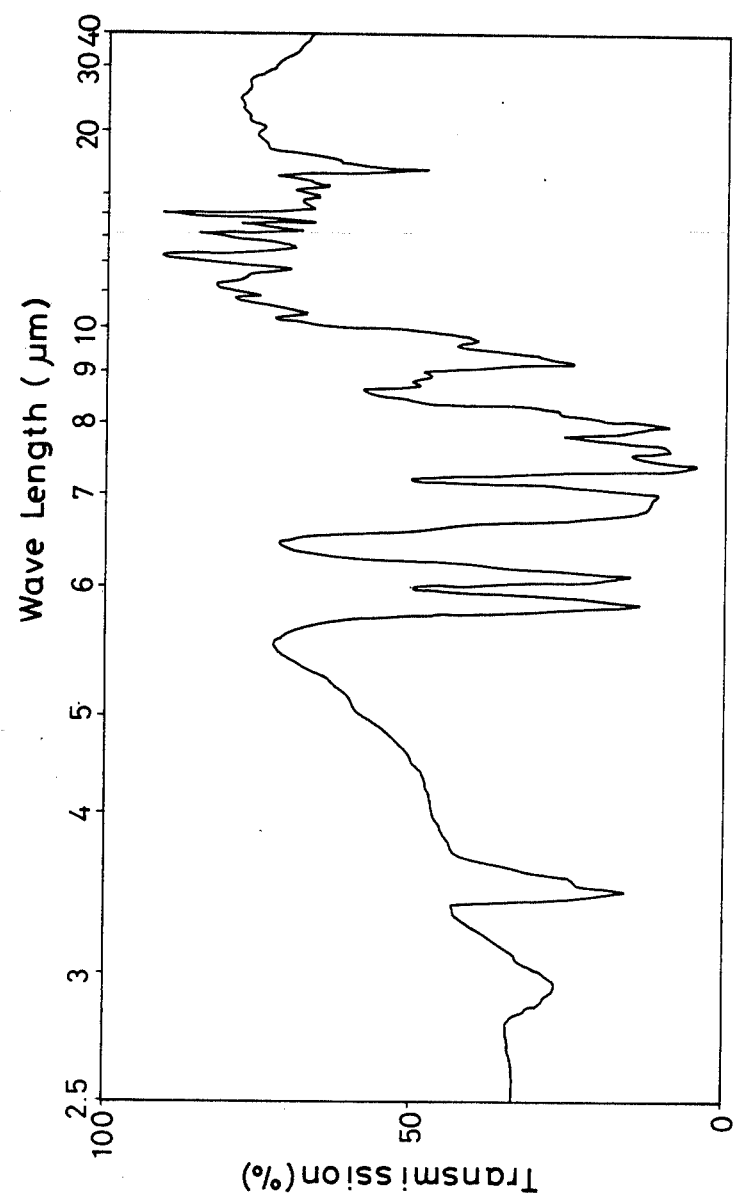
Figure 18:
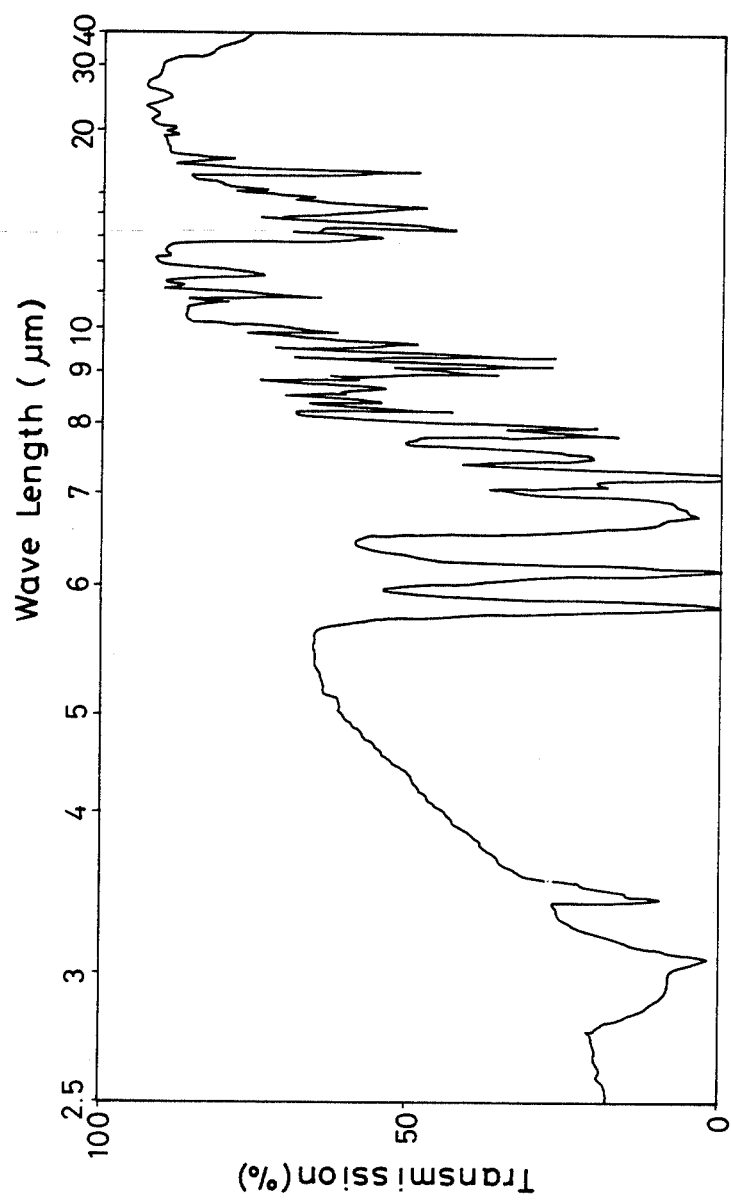
Figure 19:
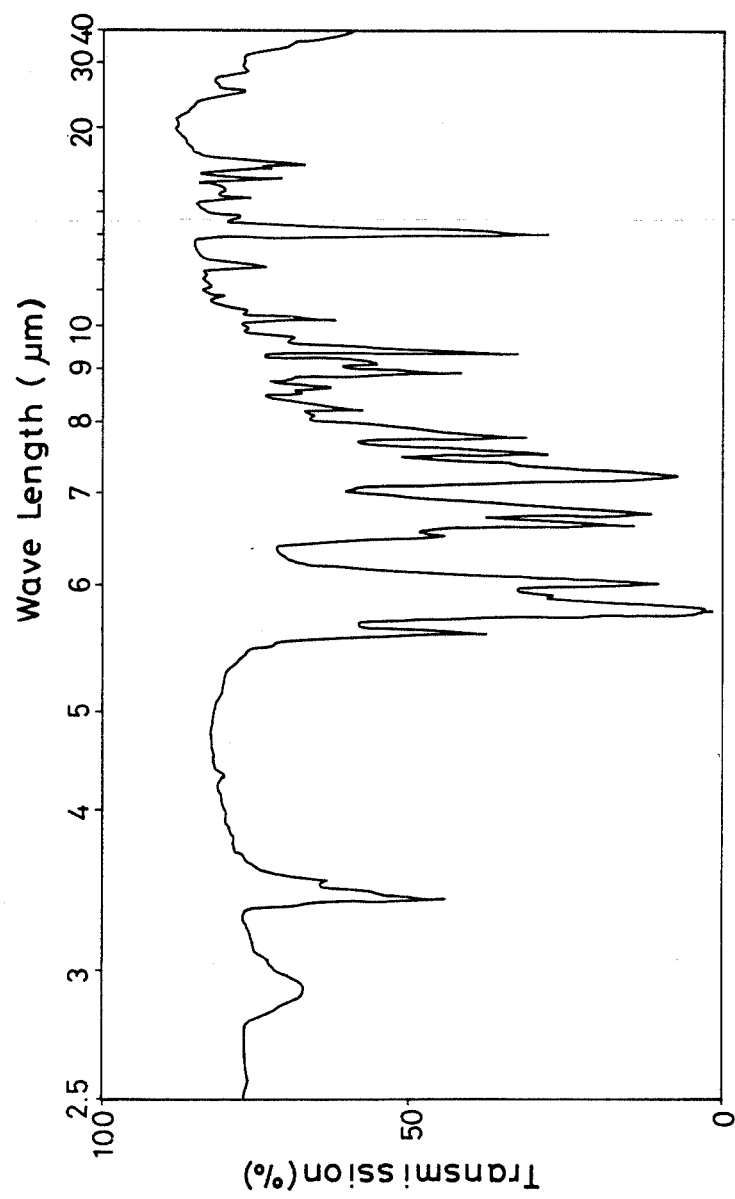
Figure 20:
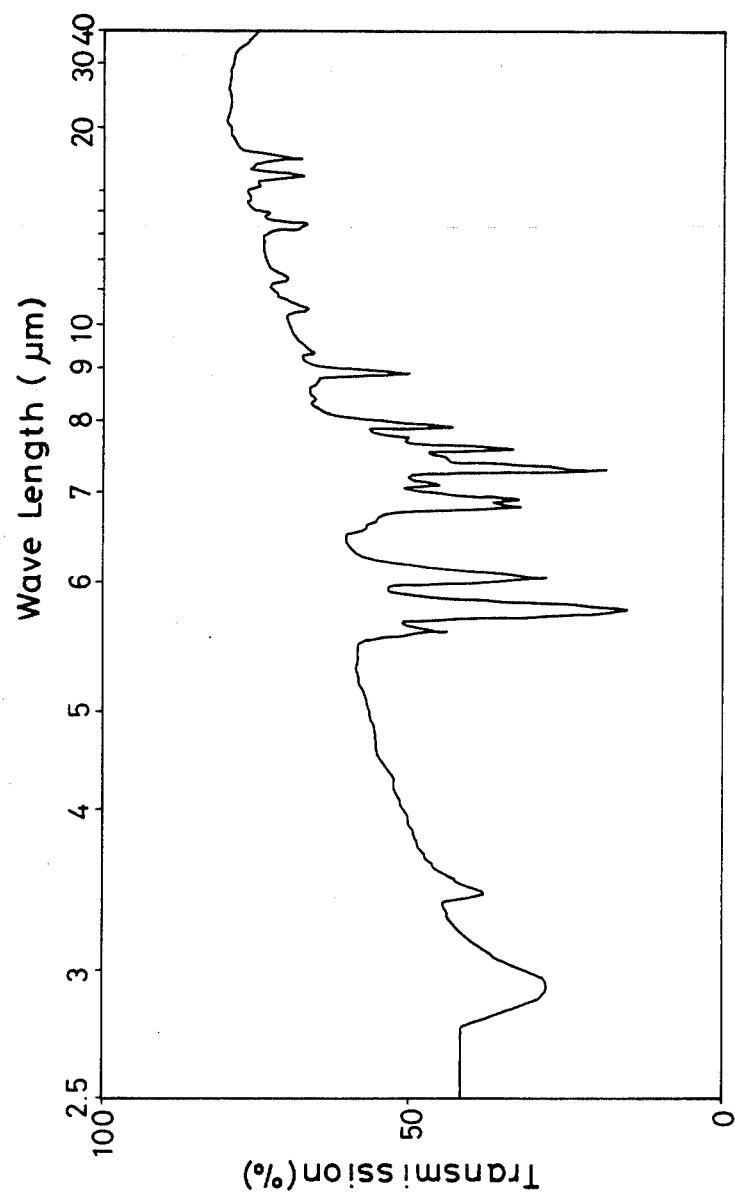
Figure 21:
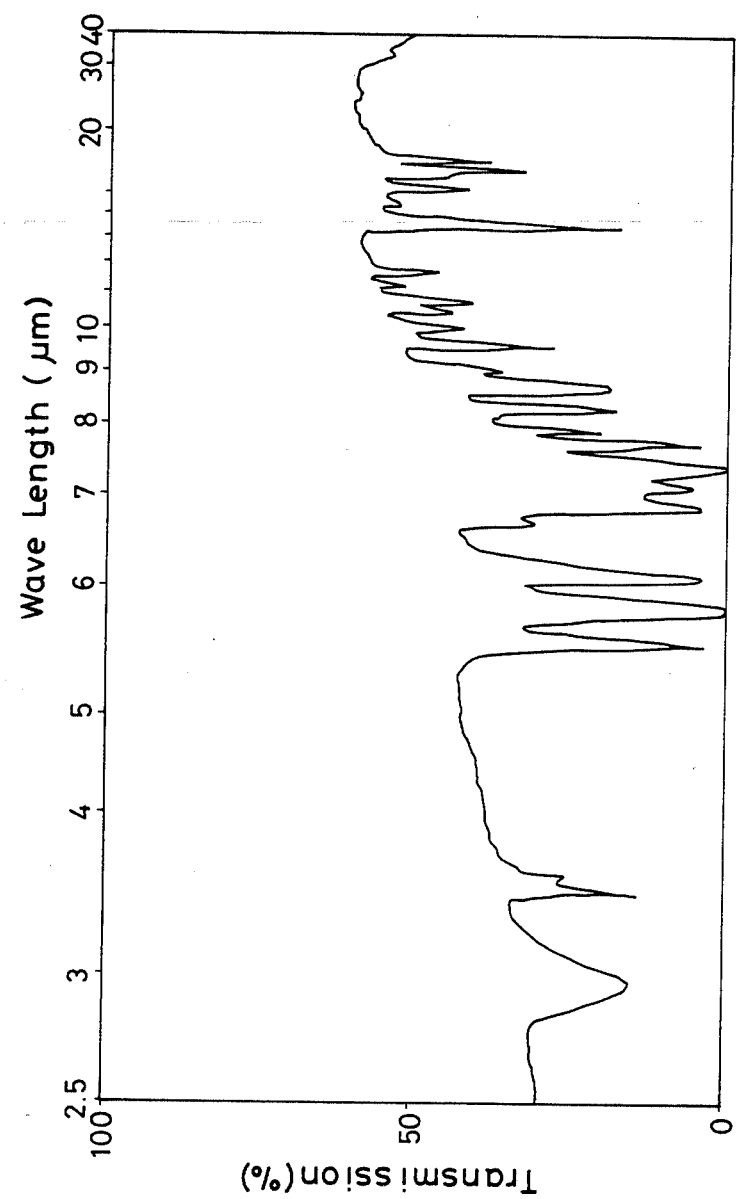
Figure 22:
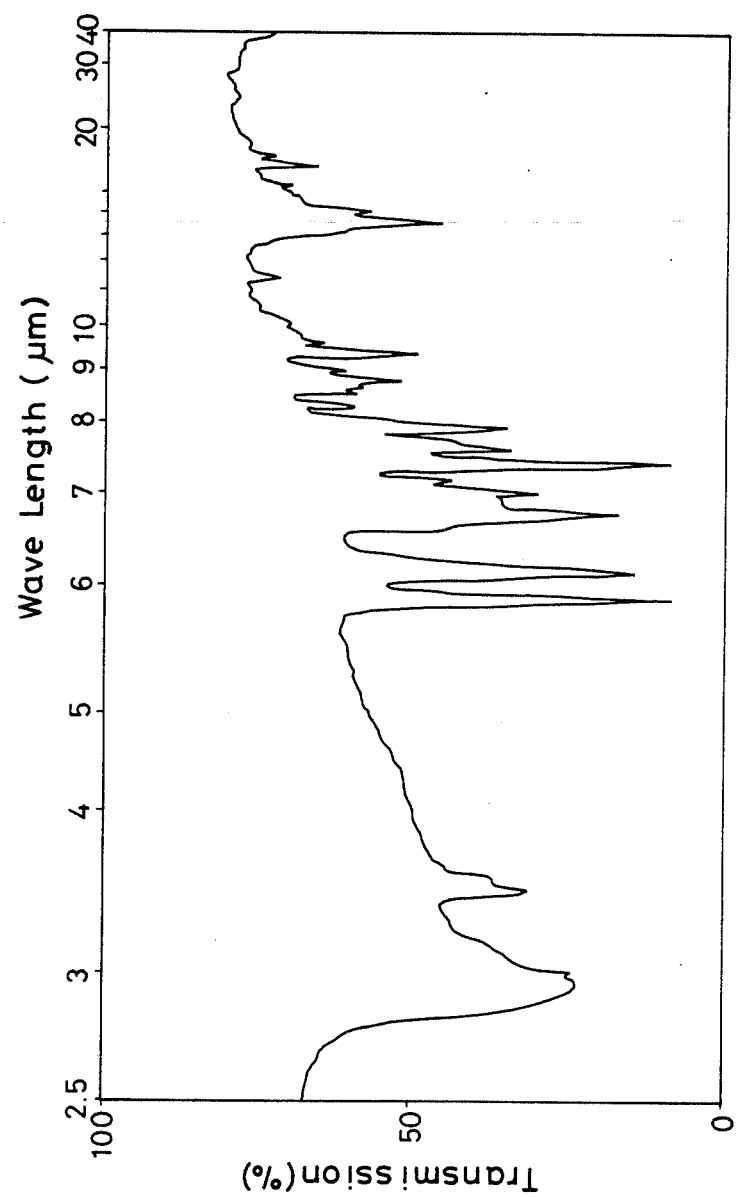
Figure 23:
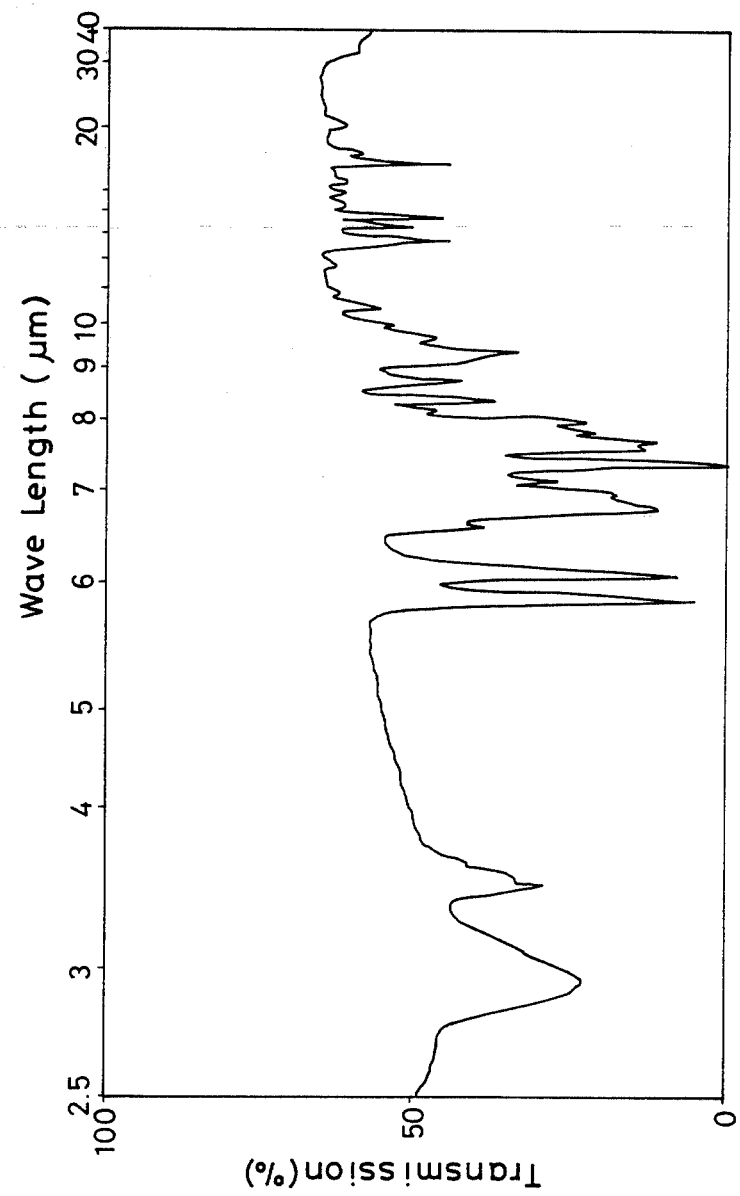
Figure 24:
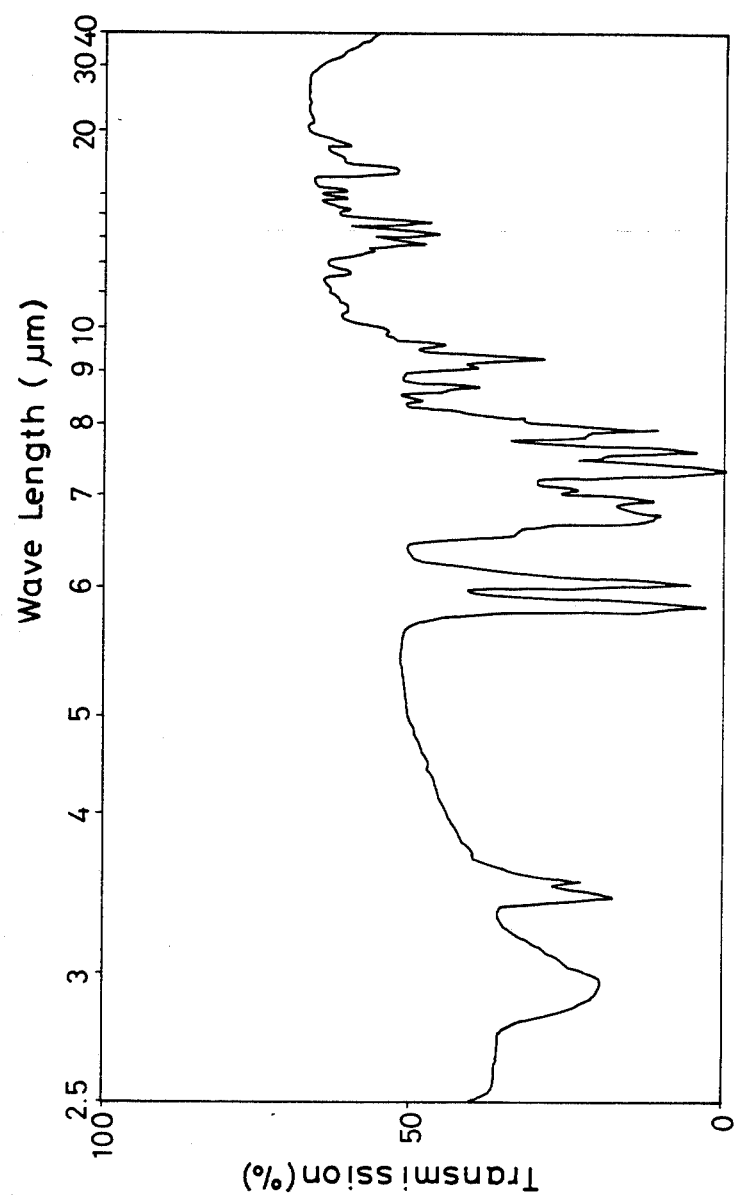
Figure 25:
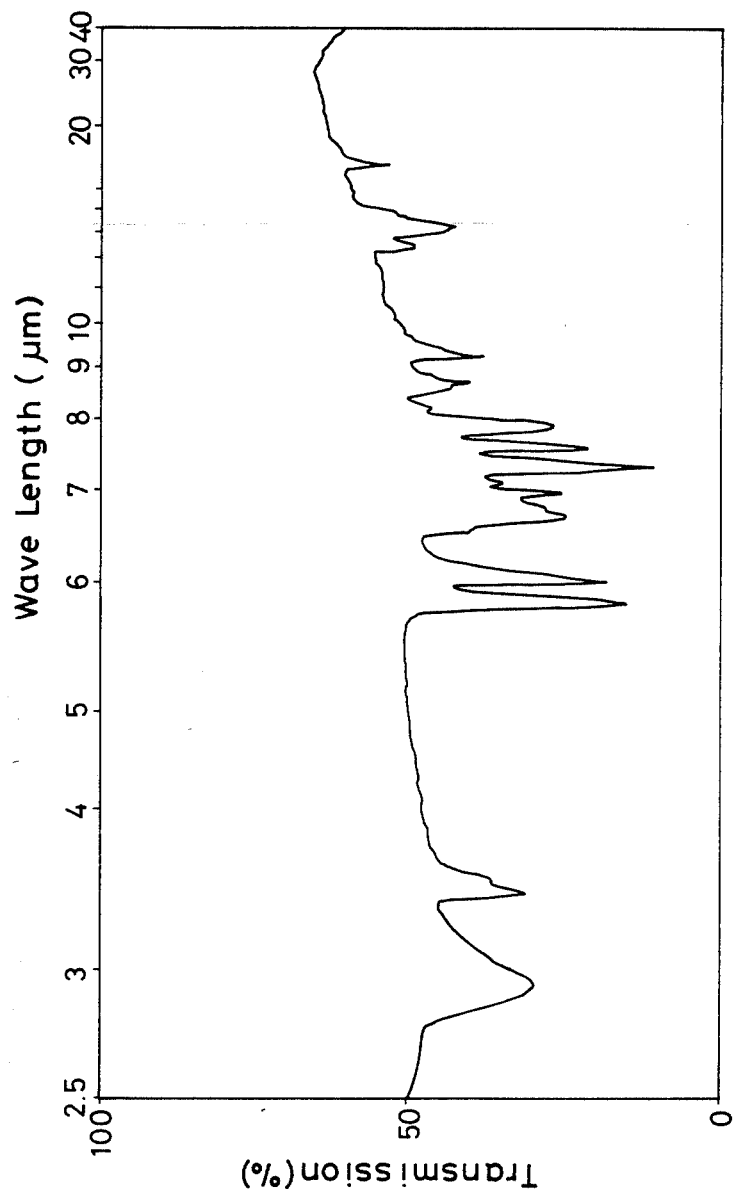

| Number of the present compound | Substituents in the formula (I) | | Melting point (°C.) | Yield (%) | Infrared spectrum |
|---|---|---|---|---|---|
| | $R^1$ | $R^2$ | | | |
| 1 | $CH_3$— | $CH_3$— | 175 to 176 | 58 | FIG. 1 |
| 2 | $CH_3CH_2CH_2$— | $CH_3$— | 136 to 138 | 93 | FIG. 2 |
| 3 | $CH_3$— | $(CH_3)_2CH$— | 170 to 172 | 73 | FIG. 3 |
| 4 | $CH_3CH_2CH_2$— | $(CH_3)_2CH$— | 121 to 123 | 68 | FIG. 4 |
| 5 | $CH_3$— | $(CH_3)_3C$— | 186 to 187 | 95 | FIG. 5 |
| 6 | $(CH_3)_2CH$— | $(CH_3)_3C$— | 163 to 164 | 63 | FIG. 6 |

The present invention will be explained more in detail while referring to Examples as follows.

However, the present invention is not to be restricted to Examples under-mentioned. From the foregoing description, one skilled in the art can easily ascertain the essential characteristics of the present invention, and without departing from the spirit and scope thereof, can make various changes and modifications of the present invention to adapt it to various usages and conditions.

For reference, the NMR spectra of the present compounds are measured while using TMS as the internal standard, and the representative patterns are shown by the following marks.

S means singlet, d means doublet, t means triplet, 6-plet means sextet and m means multiplet.

EXAMPLE 1

Synthesis of
Tetrahydro-1-methyl-3-(4,5,6,7-tetrahydro-5-methyl-7-oxo-2-benzothiazolyl)-5-propyl-1,3,5-triazine-2(1H)-one (Compound No. 2)

To a solution of 1.5 g (0.0063 mol) of N-methyl-N'-(4,5,6,7-tetrahydro-5-methyl-7-oxo-2-benzothiazolyl)urea in 20 ml of dimethylformamide, 1.8 ml of aqueous 35% solution of formaldehyde (0.021 mol) were added, and the mixture was stirred for 30 min at room temperature. After adding 0.37 g (0.0063 mol) of propylamine to the mixture, the whole mixture was stirred for 18 hours at room temperature and further for 3 hours at 90° C.

The solid material obtained by distilling off the solvents and volatile substances from the mixture was recrystallized from ethanol to obtain 1.55 g of yellow crystals (yield: 93% and M.P.: 138° C.) showing the following spectra.

IR(as KBr tablet) cm$^{-1}$: $\nu_{CO}$ 1670 and 1640.

NMR(in CDCl$_3$)$\delta$ ppm: 0.97(3H, t, J=7 Hz, 5-CH$_2$CH$_2$CH$_3$); 1.22(3H, bs, 5'-CH$_3$); 1.58(2H, 6-plet, J=7 Hz, 5-CH$_2$CH$_2$CH$_3$); 2.10 to 2.58(5H, 4'-H$_2$, 6'-H$_2$ and 5'-H); 2.73(2H, t, J=7 Hz, 5-CH$_2$CH$_2$CH$_3$); 3.02(3H, s, 1-CH$_3$); 4.32(2H, s, 6-H$_2$) and 5.15(2H, s, 4-H$_2$).

EXAMPLE 2

Synthesis of
Tetrahydro-1,5-dimethyl-3-(4,5,6,7-tetrahydro-7-oxo-5-isopropyl-2-benzothiazolyl)-1,3,5-triazine-2(1H)-one (Compound No. 3)

To a solution of 3.4 g (0.013 mol) of N-methyl-N'-(4,5,6,7-tetrahydro-7-oxo-5-isopropyl-2-benzothiazolyl)urea in 20 ml of dimethylformamide, 3.6 ml of aqueous 35% solution of formaldehyde (0.042 mol) were added, and after stirring the mixture for 30 min at room temperature, 1.9 ml of aqueous 40% solution of methylamine (0.025 mol) was added to the mixture, and the whole mixture was stirred for 30 min at room temperature and further for one hour at 70° to 80° C. Then, the reaction mixture was poured into water, and the thus appeared crystalline precipitate was collected by filtration and recrystallized from ethanol to obtain 2.9 g of pale yellow crystals (yield: 73% and M.P.: 170° to 172° C.).

The product showed the following spectra.
IR (as KBr tablet, cm$^{-1}$): $\nu_{CO}$ 1640.
NMR(in CDCl$_3$, $\delta$ ppm): 1.00

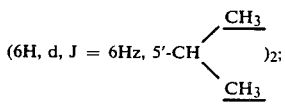

1.36 to 3.30(6H, m, 4'-H$_2$, 6'-H$_2$, 5'-H and 5'CH(CH$_3$)$_2$); 2.70(3H, s, 5-CH$_3$); 3.07(3H, s, 1-CH$_3$); 4.39($\overline{2H}$, s, 6-H$_2$) and 5.22(2H, s, 4-H$_2$).

The following is some of Preparation Example, wherein the carrier (diluent), the adjuvant, the ration of mixing thereof and the active ingredient may be changed in a broad range.

PREPARATION EXAMPLE 1

Preparation and Use of a Wettable Powder

By mixing 50 parts by weight of the present compound (Compound No. 1), 5 parts by weight of a salt of ligninsulfonic acid, 3 parts by weight of a salt of alkylsulfonic acid and 42 parts by weight of diatomaceous earth, and pulverizing the mixture, a wettable powder was prepared.

The thus prepared wettable powder is applied after diluting thereof with water to a suitable concentration of the present compound (Compound No. 1) as the active ingredient.

PREPARATION EXAMPLE 2

Preparation and Application of an Emulsifiable Concentrate

By uniformly mixing 25 parts by weight of the present compound (Compound No. 3), 65 parts by weight of xylene and 10 parts by weight of polyoxyethylenealkyl aryl ether, an emulsifiable concentrate was prepared. The thus prepared emulsifiable concentrate is applied after diluting thereof with water to a suitable concentration of the present compound (Compound No. 3) as the active ingredient.

PREPARATION EXAMPLE 3

Preparation and Application of a Granular Composition

After uniformly mixing 8 parts by weight of the present compound (Compound No. 5), 40 parts by weight of bentonite, 45 parts by weight of clay and 7 parts by weight of a salt of ligninsulfonic acid, the mixture was kneaded with water and processed into granules by an extruding granulator. The granules were dried and sifted to be a product of granular composition which is directly applied.

The effectiveness of the present compounds is explained while referring to the herbicidal test examples as follows.

HERBICIDAL TEST EXAMPLE 1

On the foliage of each of the following plants grown from their seeds under a management in a plastic planter of 180×580×150 mm in size, each of the wettable powders prepared as in Preparation Example 1 and diluted to 0.1 part by weight of the active ingredient with water was sprayed by a small pressured-sprayer at a rate of 10 liters per are (100 m$^2$). After spraying, the plastic planters were placed in a greenhouse.

After 21 days of the treatment, the state of the plants in the planter was observed to assess the damage due to the application of each of the wettable powders to find out the herbicidal activity thereof according to the following criteria.

| Criteria of Herbicidal Activity | |
|---|---|
| Index | Phytotoxicity |
| 0 | none |
| 1 | very slight |
| 2 | slight |
| 3 | moderate |
| 4 | severe |
| 5 | very severe (plants withered) |

| Name of the plants tested | |
|---|---|
| 1. Echinochloa crus-galli | 2. Digitaria ciliaris |
| 3. Poa annua | 4. Cyperus iria |
| 5. Chenopodium album | 6. Stellaria media |
| 7. Cardamine flexuosa | 8. Portulaca oleracea |
| 9. Glycine max (Soybean) | 10. Zea mays (maize) |
| 11. Triticum aestivum (wheat) | |

The herbicidal activities of the present compounds thus assessed are shown in Table 2. The growth state of the plants when the present wettable powders were applied was the 2 to 4-leaf-stage.

TABLE 2

| Plant | Herbicidal Activity Present Compound No. | | | | | | Not treated |
|---|---|---|---|---|---|---|---|
| | 1 | 2 | 3 | 4 | 5 | 6 | |
| Echinochloa crus-galli | 3 | 4 | 3 | 3 | 4 | 4 | 0 |
| Digitaria ciliaris | 5 | 5 | 4 | 4 | 5 | 5 | 0 |
| Poa annua | 5 | 5 | 3 | 5 | 5 | 5 | 0 |
| Cyperus iria | 2 | 2 | 1 | 1 | 3 | 3 | 0 |
| Chenopodium album | 5 | 5 | 3 | 3 | 5 | 5 | 0 |
| Stallaria media | 5 | 5 | 5 | 5 | 5 | 5 | 0 |
| Cardamine flexuosa | 5 | 5 | 5 | 5 | 5 | 5 | 0 |
| Portulaca oleracea | 5 | 4 | 3 | 2 | 5 | 5 | 0 |
| Glycine max (soy-bean) | 1 | 0 | 0 | 0 | 1 | 1 | 0 |
| Zea mays (maize) | 0 | 0 | 0 | 0 | 0 | 0 | 0 |
| Triticum aestivum (wheat) | 1 | 0 | 1 | 0 | 0 | 0 | 0 |

What is claimed is:

1. A tetrahydrobenzothiazole represented by the formula (I):

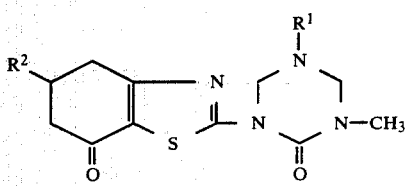

wherein $R^1$ and $R^2$ represent respectively a straight-chain alkyl group having 1 to 6 carbon atoms or a branched-chain alkyl group having from 3 up to and including 6 carbon atoms.

2. Tetrahydro 1-methyl-3-(4,5,6,7-tetrahydro-5-t-butyl-7-oxo-2-benzothiazolyl)-5-methyl-1,3,5-triazine-2(1H)-one.

3. Tetrahydro 1-methyl-3-(4,5,6,7-tetrahydro-5-t-butyl-7-oxo-2-benzothiazolyl)-5-isopropyl-1,3,5-triazine-2(1H)-one.

4. A herbicidal composition comprising a herbicidally effective amount of a tetrahydrobenzothiazole derivative represented by the formula (I):

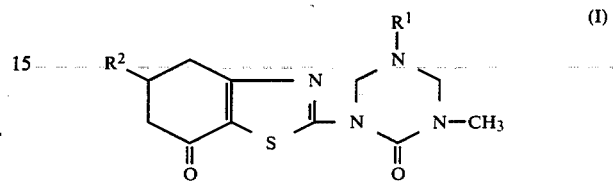

wherein $R^1$ and $R^2$ represent respectively a straight-chain alkyl group having 1 to 6 carbon atoms or a branched-chain alkyl group having from 3 up to and including 6 carbon atoms, and a diluent therefor.

5. A herbicidal composition according to claim 4, wherein said derivative is tetrahydro-1-methyl-3-(4,5,6,7-tetrahydro-5-t-butyl-7-oxo-2-benzothiazolyl)-5-methyl-1,3,5-triazine-2(1H)-one.

6. A herbicidal composition according to claim 4, wherein said derivative is tetrahydro-1-methyl-3-(4,5,6,7-tetrahydro-5-t-butyl-7-oxo-2-benzothiazolyl)-5-isopropyl-1,3,5-triazine-2(1H)-one.

* * * * *